United States Patent
Cameron et al.

(10) Patent No.: US 8,052,424 B2
(45) Date of Patent: Nov. 8, 2011

(54) METHOD FOR MAKING A DENTAL RESTORATION

(75) Inventors: Tom Cameron, Medford, NJ (US); Vicky Nemzer, Newton, PA (US); Al McDonald, Wallingford, PA (US); Arlo King, Lumberton, NJ (US); Christopher Chu, West Windsor, NJ (US); Slawomir Banasiak, Kearny, NJ (US)

(73) Assignee: Dentsply International, Inc., York, PA (US)

( * ) Notice: Subject to any disclaimer, the term of this patent is extended or adjusted under 35 U.S.C. 154(b) by 710 days.

(21) Appl. No.: 12/070,076

(22) Filed: Feb. 14, 2008

(65) Prior Publication Data

US 2009/0061390 A1    Mar. 5, 2009

(51) Int. Cl.
*A61C 13/083*    (2006.01)
*A61C 19/10*    (2006.01)
*A61C 13/09*    (2006.01)
*A61C 13/08*    (2006.01)
*A61C 5/10*    (2006.01)

(52) U.S. Cl. .................... 433/223; 433/26; 433/203.1

(58) Field of Classification Search .............. 433/223, 433/26, 202.1, 203.1, 212.1, 218, 222.1; 427/2.1, 2.16, 2.29, 8; 264/16–20; 106/35
See application file for complete search history.

(56) References Cited

U.S. PATENT DOCUMENTS

| | | | | |
|---|---|---|---|---|
| 3,507,042 A * | 4/1970 | Hana | ............................... | 433/26 |
| 4,207,678 A * | 6/1980 | Jeannette | ................... | 433/203.1 |
| 4,380,435 A * | 4/1983 | Raeder et al. | ................. | 433/180 |
| 4,608,015 A * | 8/1986 | Smigel | ............................. | 433/26 |
| 4,620,841 A * | 11/1986 | Farrell et al. | ..................... | 433/26 |
| 4,828,117 A * | 5/1989 | Panzera et al. | .............. | 206/63.5 |
| 5,127,835 A * | 7/1992 | Yamaguchi et al. | ........ | 433/222.1 |
| 5,257,931 A * | 11/1993 | Pozzi | .............................. | 433/26 |
| 5,588,834 A * | 12/1996 | Resk et al. | ...................... | 433/26 |
| 6,030,209 A * | 2/2000 | Panzera et al. | ................. | 433/26 |
| 6,033,222 A * | 3/2000 | Schneider et al. | ......... | 433/203.1 |
| 6,315,554 B1 * | 11/2001 | Coste et al. | ..................... | 433/26 |
| 6,328,563 B1 * | 12/2001 | Hobo | .............................. | 433/26 |
| 6,802,714 B2 * | 10/2004 | Cruz | ............................... | 433/26 |
| 2003/0031984 A1 | 2/2003 | Rusin et al. | | |
| 2003/0124481 A1 * | 7/2003 | Zun | ................................ | 433/26 |
| 2003/0235799 A1 * | 12/2003 | Cruz | ............................... | 433/26 |
| 2005/0095554 A1 * | 5/2005 | Wilkinson | ...................... | 433/76 |
| 2005/0132928 A1 * | 6/2005 | Culp | ............................... | 106/35 |
| 2008/0199826 A1 * | 8/2008 | Jia et al. | ......................... | 433/26 |
| 2010/0173257 A1 * | 7/2010 | Yamamoto et al. | ............. | 433/26 |

* cited by examiner

*Primary Examiner* — Todd Manahan
*Assistant Examiner* — Michael R Ballinger
(74) *Attorney, Agent, or Firm* — Douglas J. Hura; David A. Zdurne; Leana Levin

(57) ABSTRACT

A series of ceramic ingots is provided in which each ingot in the series, referred to as base ingots, has a shade corresponding to a different shade of a shade guide. The number of differently shaded base ingots is less than the total number of shades associated with the shade guide. A base ingot is selected from the series having a shade of a value at least as high as a shade associated with a patient's tooth. If the base ingot shade matches the patient's tooth, a restoration made with the selected base ingot can be glazed as is; otherwise the dental restoration is stained with a stain having a lower value than the selected base ingot to match the tooth. Thus, the total different number of ingot shades needed in inventory is reduced but without requiring staining in every case.

5 Claims, No Drawings

METHOD FOR MAKING A DENTAL RESTORATION

FIELD OF THE INVENTION

The present invention is directed to dental restorations and more particularly to kits and methods for producing dental restorations of a desired shade.

BACKGROUND OF THE INVENTION

Dental restorations are created by a number of techniques. One particularly popular technique is the pressable technique in which a ceramic ingot is heated and pressed using the lost wax process to create a dental restoration that can be permanently placed in a patient's mouth.

Natural and artificial teeth come in a variety colors. If a dental restoration does not match very closely to a patient's natural tooth color, the fact that the patient has a restoration is readily apparent. This is undesirable because it does not produce the aesthetically pleasing result sought by many dental patients.

Shade guides have been developed that establish a finite number of shades to which a patient's tooth can be matched so that a suitable restoration can be produced. One particularly popular and still widely used shade guide is the Vita® Classic shade guide introduced in 1956 by Vita Zahnfabrik AG of Germany. The Vita Classic shade guide consists of 16 separate shades divided by hue into four families identified as A through D. Each family is then further divided into four subdivisions, each numbered 1 through 4. The subdivisions are numbered in order of decreasing value (lightness or darkness) and increasing chroma (intensity of color).

Current pressable dental restoration systems generally require using a different shade of ingot for each of the different shades represented on shade guide. While this gives a satisfactory final restoration product, it is inefficient for dental laboratories that make the restorations. For example, dental laboratories must keep a ready inventory of ingots for each of the 16 shades represented by the Vita Classic shade guide on hand, many of which are less popular than others. A glaze is then usually applied and fired to the restoration to impart a glassy appearance.

Other existing pressable restoration systems provide a limited number of neutral colored ingots to which two, three or more layers of low chroma shade stain must be applied and fired instead of glazing. While this may reduce the inventory of ingot types needed by a laboratory, this process still lacks efficiency because the neutral ingots do not correspond to any shades of the shade guide; thus the restoration must always be stained to achieve the desired end result. Additionally, staining may result in a slightly less aesthetic restoration than restorations that are glazed over an already properly shaded restoration.

What is needed is a more efficient method for making dental restorations that correspond to the shade of a patient's tooth that reduces a laboratory's need for a full set of different shades of ingots in its on-hand inventory, while still providing a high percentage of restorations that can be glazed as part of the finishing process.

What is also needed is a more efficient method for making those dental restorations that do need to be stained, avoiding the need for applying and firing multiple layers of stains.

SUMMARY OF THE INVENTION

The invention relates to a method of making dental restorations. The method includes providing a series of ceramic ingots in which each ingot in the series, referred to as base ingots, has a shade corresponding to a different shade of a shade guide. The number of differently shaded base ingots in the provided series is less than the total number of shades associated with the shade guide. The method also includes selecting a base ingot from the series having a shade of a value at least as high as a shade associated with a patient's tooth and using the ingot to make a dental restoration. If the base ingot used to make the dental restoration corresponds to the shade associated with the patient's tooth, a glaze is applied to the dental restoration. If the base ingot used to make the dental restoration does not correspond to the shade associated with the patient's tooth, the dental restoration is stained with a stain having a lower value than the selected ingot. According to one embodiment of the invention, if a stain is required, a single application and firing results in the final desired shade.

The invention also relates to a kit. The kit includes a series of ceramic base ingots. Each ingot in the series has a shade corresponding to a different shade of a shade guide and the number of different shades of ingots in the provided series is less than the total number of shades associated with the shade guide. The kit also includes instructions for using the base ingots from the series with unique combinations of opaques and stains to produce a finished dental restoration having a shade corresponding to any shade in the shade guide.

One advantage of exemplary embodiments of the invention includes providing a limited number of ingots of different shades that can be used to make a full set of shades corresponding to a shade guide, thereby limiting the breadth of on-hand inventory of differently shaded ingots a dental laboratory needs.

Another advantage of exemplary embodiments of the invention is that the base ingots in the series may be selected so that a majority of dental restorations are made with an ingot corresponding to the same shade as the finished restoration and thus can be glazed instead of stained to achieve the final color match.

Yet another advantage of exemplary embodiments of the invention includes that in situations in which the dental restoration does need to be stained as part of the finishing process, the staining can be achieved in a single application and firing, avoiding the need for multiple separate application and firing steps.

Still another advantage of the invention is the ability to achieve multiple shades of restorations from a single pressing cycle.

Other features and advantages of the present invention will be apparent from the following more detailed description of the exemplary embodiments which illustrate, by way of example, the principles of the invention.

DETAILED DESCRIPTION OF EXEMPLARY EMBODIMENTS

Exemplary embodiments of the invention are discussed below with respect to a press-to-metal dental restoration system. However, it will be appreciated that the invention is not so limited and the principles are applicable to any method of making a dental restoration in which a final restoration will be color matched to a patient's tooth, including methods of making dental restorations using press-to-zirconia systems, all-ceramic pressable systems, and that may even be applied with respect to stackable porcelain techniques. It will further be appreciated that embodiments of the invention can be used for the production of any type of dental restoration, and is particularly useful for prostheses such as crowns, bridges, and veneers, by way of example only.

Likewise, while exemplary embodiments of the invention are discussed with respect to the Vita® Classic shade guide, the principles of the invention may similarly be applied for use with other shade guides, for example, the Illumine'™ shade guide from Dentsply International Inc. which may be used in combination with or to supplement the Vita Classic shade guide for bleached teeth. Other exemplary shade guides include Vita® Lumin and Vita® 3D Master from Vita Zahnfabrik AG and Portrait® and Bioform®, both available from Dentsply International Inc.

As part of ordering a patient's dental restoration, a dentist ordinarily compares the tooth to be restored, as well as surrounding teeth, to a shade guide. The dentist selects the shade from the shade guide that most closely resembles the color of the patient's teeth so that a restoration can be produced in a shade that will match as closely as possible, or alternatively that may be identified to achieve a desired cosmetic effect. Thus, the prescription that a dentist sends to a dental laboratory generally includes the shade in which the restoration should be produced along with an impression of the patient's teeth and any other information that may be needed by the laboratory to make the restoration.

Shade guides of a relatively few finite number of shades have been developed to standardize and simplify communication between dentists and laboratories. The most commonly used shade guide is the Vita® Classic shade guide, consisting of 16 different shades A1 to D4, as described above.

In making a press-to-metal dental restoration, such as those made using the Ceramco®. Press system, available from Dentsply International Inc. of York, Pa., an alloy substructure of the dental restoration is first formed in the ordinary manner as known to those of ordinary skill in the art. Preferably, the alloy is a high noble, noble or predominantly base alloy and has a melt range at or above 1000° C.

An opaque porcelain, typically in powder or paste form, is applied to the metal substructure. The opaque is then dried and fired in accordance with known techniques. In accordance with exemplary embodiments of the invention, the shade of the opaque porcelain is typically selected to correspond to the final shade of the restoration. Thus, for example, if the prescription indicates that the final restoration should correspond to B4 on the Vita Classic shade guide, a B4 opaque porcelain should be used. One suitable opaqueing porcelain includes, by way of example only, Ceramco® Press opaqueing porcelains, also available from Dentsply. Generally, two applications of opaque porcelain are needed to completely mask the metal substructure, which is desired to achieve an aesthetically pleasing end product. In embodiments which do not use a metal substructure, the opaqueing step may be omitted or another layering technique may be used in its place.

Once the opaqued substructure has been fired, a wax-up of the restoration is created on the substructure, typically using either the full contour or cut-back technique. In accordance with the well-known lost wax technique, the waxed substructure is sprued and invested, after which the wax is burned out. These steps result in a mold in the shape of the restoration to be formed that is defined by the metal substructure and investment material. A heated ceramic ingot is then pressed into the mold to produce the restoration.

In accordance with exemplary embodiments of the invention, it is not necessary to provide ingots corresponding directly to each different shade of the shade guide as found in conventional pressing systems. It has been discovered that a series of limited number of ingots can meet this need by organizing the shades of the shade guide by value. In doing so, the number of shades of ingots needed to make any of a the full set of different shades is substantially reduced. This results in a more efficient process and reduces the number of different types of ingots that a laboratory must have on hand to fulfill orders in a timely fashion.

Thus, according to an exemplary embodiment of the invention, a series of a limited number of differently shaded ingots is provided in which the number of shades provided is less than the total number of different shades in the shade guide. That is, unlike the usual full complement of ingots currently provided and individually used to produce different shades, by providing a series of ingots sorted by value, only a few selected base ingots, designated herein as a "value series," are needed to produce restorations across a full set of shades when used in combination with subsequent staining when needed to achieve darker values.

For example, according to one embodiment of the invention, a series of only 5 different shades of base ingots are used to produce restorations that match all 16 Vita Classic shades. According to another embodiment of the invention, a single ingot bleach shade base ingot is used to produce 4 Illumine' shades (I1 through I4) for patients with bleached teeth that may be provided with or separately from the base ingots to match the 16 Vita shades.

The 16 classic Vita shades and (optionally the 4 Illumine' shades) are divided into 5 (optionally 6) groups by value, i.e. each shade in a group has a similar value (or lightness) and, therefore, can be produced from one ingot of the highest value, as illustrated in a table below:

| Value Series (VS) Base Ingot | | Resulting Shades that can be produced from the base ingot with Shade Stains | Base ingot Shade |
|---|---|---|---|
| VS0 | | I4, I3, I2, I1 | I3 |
| VS1 | | B1, A1, B2 | B1 |
| VS2 | Value | A2, D3 | A2 |
| VS3 | Decreases | C1, C2, D2, D4 | C1 |
| VS4 | | A3, B3, B4, C3 | A3 |
| VS5 | | A3.5, A4, C4 | A3.5 |

Value Decreases →

As shown in the table, the base ingots selected for the value series correspond to an actual shade on the shade guide; the base ingots are generally, but not necessarily, the lightest value in each group. For example, VS1 base ingot has a B1 shade, VS2=A2, VS3=C1, VS4=A3 and VS5=A3.5. The only exception in the preferred embodiment is with respect to the bleach shade base ingot, VS0, in which VS0=I3, which is a lower value than I4; the final shade of I4 is accomplished by using an opaque higher in value than I4 in combination with the I3 shaded ingot.

Thus, the base ingot to be used in the restoration is generally selected by choosing the base ingot which has a value equal to or higher than the final shade for the finished restoration, but which is not lower than the next lowest value base ingot. By selecting the base ingot of the lightest shade in the group as the base ingot, lower value (i.e. darker) shades can be created by applying a surface stain to the restoration. With respect to the VS1 group, for example, a B1 shaded ingot can be used to produce any one of a B1, an A1, or a B2 shaded final restoration when used in combination with a suitable stain. By way of further example, A1 has a lower value than B1, but is produced from a VS1 (i.e., B1) base ingot. The final A1 shade for the restoration results from subsequent staining of the restoration with A1 dentin shade stain, as discussed in more detail below. Thus, to produce an A1 restoration for a patient having an A1 prescription, the restoration has an A1 opaque on the metal substructure to which a B1 ingot is pressed, followed by application of an A1 dentin shade stain.

Furthermore, where possible, the base ingots may be selected to correspond with the most common shades. As a result, in many cases the base ingots from the value series can be glazed in the ordinary fashion without needing stain. Thus, efficiency is increased because the laboratory would have on hand the most popular ingots, which in many cases, would not require staining. Put another way, the base ingots for the value series may be, but are not necessarily, selected to correspond with the most common shade within a grouping.

For example, it may be possible to make an A2 restoration in one of two ways. A VS1 base ingot could be stained to achieve the lower value A2 shade. However, because A2 happens to be a particularly common shade, it has been identified as a base ingot in the value series. As a result, an A2 restoration can also be pressed directly from a VS2 ingot. According to the preferred embodiment of the invention, by organizing the value series as illustrated in the table above, the shades of the base ingots correspond directly to more than 50% of the shade demand, decreasing the instances in which a stain needs to be applied to achieve the desired shade in the finished restoration. Thus, a dental lab can decrease its inventory of ingots for its least used shades, while still maximizing the number of restorations that can be glazed, not stained, to provide what is generally considered a more desirable aesthetic result.

Once the ingot has been pressed, the restoration is divested and finished. In the case in which the value series base ingot corresponds directly to the final matched shade of the restoration, a glaze may be applied and fired on the dental restoration as part of the finishing procedures, after which the restoration is ready for fitting and cementing in the patient's mouth. As discussed above, according to a preferred embodiment of the invention, the restoration will generally be glazed in more than 50% of restorations produced.

In cases in which the shade of the base ingot does not correspond directly to the final shade, a stain of lower value and which corresponds to the final shade is applied to the restoration. That is, referring back to the example discussed above, if the base ingot is VS1 (i.e. corresponding to a B1 shade), but the final shade is to be A1, then an A1 dentin stain is applied and fired on the restoration. Firing the stain generally imparts substantially the same smooth glassy quality to the restoration provided by the glaze, thus an additional glaze is usually not applied after the stain has been fired.

Shade stains have not previously been widely used with pressable systems; as described above, most current systems generally involve pressing an ingot already selected to correspond directly to the final shade, which is then followed by glazing. As will be appreciated by those of ordinary skill in the art, stains generally comprise a white or clear base to which a laboratory technician adds a combination of white, tan, yellow, brown and/or gray pigments based on the desired shade to be achieved. Thus, after the stain is applied and fired, the final shade of the dental restoration corresponds to that of the prescription. However, current shade staining techniques use low chroma stains; as a result, at least two and typically three or more separate applications and firings of stain are usually needed to produce a finished restoration that has the desired final color match.

It has further been discovered by the inventors that by increasing the proportions of the pigments in the stain, a high chroma stain can be made and applied that achieves the desired color match in the finished restoration in a single application and firing step, further improving the efficiency of the restoration production process. Such high chroma stains to provide color match in a single firing are generally made by adding pigment to the base in the amount of about 8% to about 14% by weight, more typically about 10% to about 12% by weight. By contrast, low chroma stains used in dental restorations have only about 1% to about 3% by weight of pigment with respect to the stain base.

While the invention has been described with reference to the foregoing exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention.

The invention claimed is:

1. A method comprising the steps of:
providing a series of ceramic base ingots, each base ingot in the series having a shade corresponding to a different shade of a shade guide having a plurality of shades associated therewith, wherein the number of shades of base ingots in the series is less than the total number of shades associated with the shade guide;
selecting a base ingot of a shade having a value at least as high as a shade associated with a patient's tooth, wherein a lower value corresponds to a darker shade;
using the base ingot to form a dental restoration;
determining whether the shade of the dental restoration formed by the selected base ingot corresponds to the shade associated with the patient's tooth; and
in response to determining the formed dental restoration does not correspond to the shade associated with the patient's tooth, staining the formed dental restoration with a stain of a lower value than the selected base ingot.

2. The method of claim 1 wherein the step of staining comprises applying and firing a single layer of stain to the dental restoration.

3. The method of claim 1 wherein the step of selecting an ingot comprises selecting an ingot of a shade having a value at least as high as a shade associated with a patient's tooth and a value lower than the next highest value ingot in the series of ingots.

4. The method of claim 2, wherein the stain includes a base stain and about 8% to about 14% by weight pigment.

5. The method of claim 4, wherein the stain includes a base stain and about 10% to about 12% by weight pigment.

* * * * *